(12) United States Patent
Lee et al.

(10) Patent No.: US 11,185,310 B2
(45) Date of Patent: Nov. 30, 2021

(54) ULTRASOUND IMAGING APPARATUS AND CONTROL METHOD THEREOF

(71) Applicant: SAMSUNG MEDISON CO., LTD., Gangwon-do (KR)

(72) Inventors: Gun Woo Lee, Seoul (KR); SeWon Kim, Suwon-si (KR); JongHyon Yi, Yongin-si (KR); ChoongHwan Choi, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 290 days.

(21) Appl. No.: 16/235,537

(22) Filed: Dec. 28, 2018

(65) Prior Publication Data
US 2019/0200962 A1 Jul. 4, 2019

(30) Foreign Application Priority Data
Dec. 28, 2017 (KR) .......................... 10-2017-0182365

(51) Int. Cl.
*A61B 8/08* (2006.01)
*G06T 7/00* (2017.01)
(Continued)

(52) U.S. Cl.
CPC .............. *A61B 8/5207* (2013.01); *A61B 8/14* (2013.01); *A61B 8/4488* (2013.01); *A61B 8/463* (2013.01);
(Continued)

(58) Field of Classification Search
CPC ..... A61B 8/5207; A61B 8/5223; A61B 8/463; A61B 8/14; A61B 8/4488; A61B 8/469;
(Continued)

(56) References Cited

U.S. PATENT DOCUMENTS

| 9,192,358 B2 * | 11/2015 | Lee | .......................... A61B 8/06 |
| 2013/0116536 A1 * | 5/2013 | Sato | ..................... A61B 5/0095 |
| | | | 600/407 |

(Continued)

FOREIGN PATENT DOCUMENTS

| JP | 2012-210317 A | 11/2012 |
| JP | 2012-217611 A | 11/2012 |
| KR | 10-2004-0026780 A | 4/2004 |

OTHER PUBLICATIONS

Kim et al., "Quantification of Hepatorenal Index for Computer-Aided Fatty Liver Classification with Self-Organizing map and Fuzzy Stretching from Ultrasonography", BioMed Research International, vol. 2015, Article ID 535894, pp. 1-9, Jan. 1, 2015.

(Continued)

*Primary Examiner* — Joanne M Hoffman
*Assistant Examiner* — Andrew W Begeman
(74) *Attorney, Agent, or Firm* — Morgan, Lewis & Bockius LLP

(57) ABSTRACT

An ultrasound imaging apparatus includes: an image processor configured to generate an ultrasound image based on an ultrasound echo signal; a display; and a main controller configured to detect a liver area and a kidney area in the ultrasound image, extract a border line between the liver area and the kidney area, automatically establish a region of interest of the liver and a region of interest of the kidney based on the border line, obtain a diagnostic parameter for the region of interest of the liver and a diagnostic parameter for the region of interest of the kidney, and control the display to display information about the diagnostic parameter for the region of interest of the liver and the diagnostic parameter for the region of interest of the kidney.

15 Claims, 18 Drawing Sheets

(51) Int. Cl.
*G06T 7/12* (2017.01)
*A61B 8/00* (2006.01)
*A61B 8/14* (2006.01)
*G01S 15/89* (2006.01)

(52) U.S. Cl.
CPC .............. *A61B 8/469* (2013.01); *A61B 8/488* (2013.01); *A61B 8/5223* (2013.01); *G06T 7/0012* (2013.01); *G06T 7/12* (2017.01); *A61B 8/4427* (2013.01); *A61B 8/4461* (2013.01); *A61B 8/483* (2013.01); *A61B 8/5246* (2013.01); *A61B 8/54* (2013.01); *G01S 15/8979* (2013.01); *G01S 15/8993* (2013.01); *G06T 2207/10132* (2013.01); *G06T 2207/30056* (2013.01); *G06T 2207/30084* (2013.01)

(58) Field of Classification Search
CPC ..... A61B 8/488; A61B 8/4427; A61B 8/4461; A61B 8/483; A61B 8/5264; A61B 8/54; A61B 8/085; A61B 5/4244; A61B 8/00; G06T 7/0012; G06T 7/12; G06T 2207/30084; G06T 2207/30056; G06T 2207/10132; G01S 15/8979; G01S 15/8993

See application file for complete search history.

(56) References Cited

U.S. PATENT DOCUMENTS

| | | | |
|---|---|---|---|
| 2015/0073275 A1* | 3/2015 | Kanayama | A61B 8/5207 600/443 |
| 2015/0182192 A1* | 7/2015 | Kaneko | A61B 8/0891 600/427 |
| 2016/0042525 A1* | 2/2016 | Lee | A61B 8/469 382/103 |
| 2017/0091915 A1 | 3/2017 | McLaughlin et al. | |
| 2017/0258438 A1* | 9/2017 | Kanayama | A61B 8/463 |
| 2017/0273667 A1 | 9/2017 | Labyed | |
| 2017/0351836 A1 | 12/2017 | Thornton et al. | |
| 2018/0020992 A1* | 1/2018 | Guo | A61B 8/00 600/424 |

OTHER PUBLICATIONS

Extended European Search Report dated Apr. 18, 2019, issued in corresponding European Patent Application No. 18248051.7.

* cited by examiner

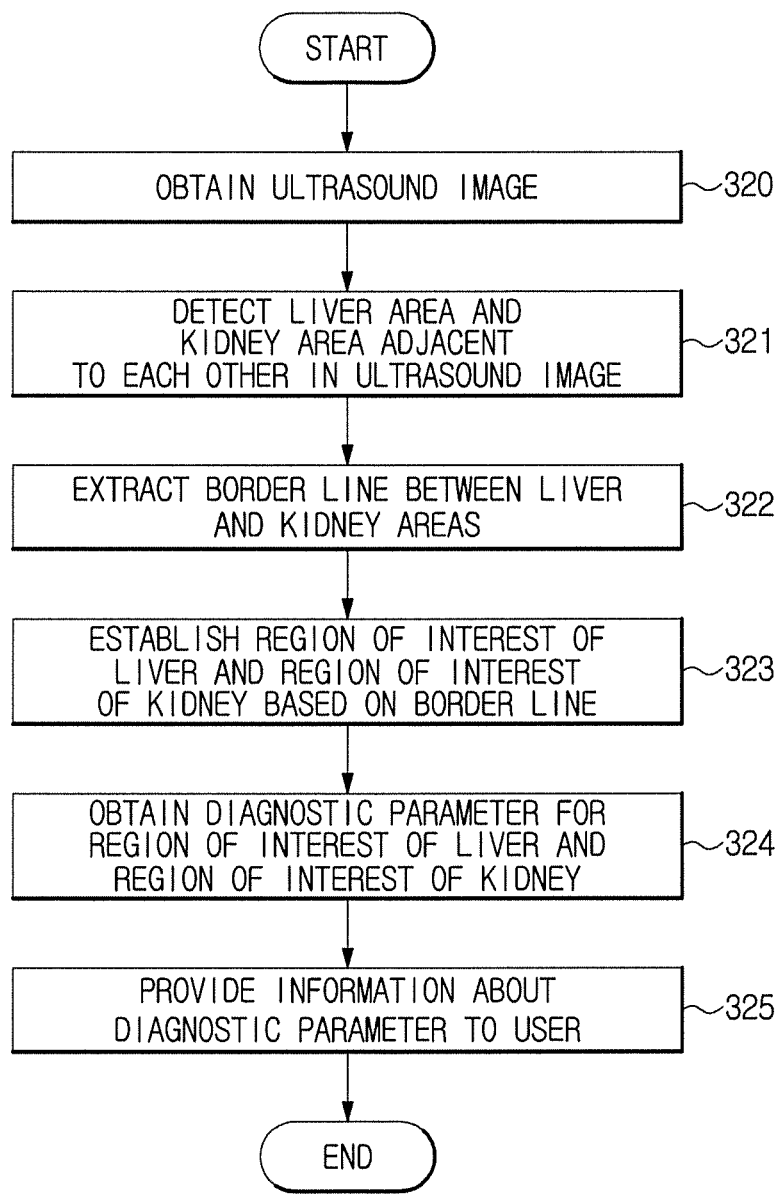

ULTRASOUND IMAGING APPARATUS AND CONTROL METHOD THEREOF

CROSS-REFERENCE TO RELATED APPLICATION

This application is based on and claims priority under 35 U.S.C. § 119 to Korean Patent Application No. 10-2017-0182365 filed on Dec. 28, 2017, in the Korean Intellectual Property Office, the disclosure of which is incorporated herein by reference in its entirety.

BACKGROUND

1. Field of the Invention

The present disclosure relates to an ultrasound imaging apparatus and control method thereof, which uses ultrasound to acquire an image of the inside of an object.

2. Discussion of Related Art

An ultrasound imaging apparatus acquires images of internal parts of an object by irradiating an ultrasound signal generated from a transducer in a probe to an object and receiving information of an echo signal reflected from the object.

The ultrasound imaging apparatus is widely used in medical diagnostic applications because it has higher stability than the X-ray imaging apparatus, is able to display images in real time, inexpensive as compared to a magnetic resonance imaging apparatus, and movable.

SUMMARY OF THE INVENTION

The present disclosure provides an ultrasound imaging apparatus and control method thereof, which may improve diagnostic reproducibility and accuracy in diagnosing a fatty liver based on ultrasound images by automatically establishing a region of interest of a liver appearing in the ultrasound image and a region of interest of another internal organ to be compared with the liver, automatically calculating diagnostic parameters for the respective regions of interest, and providing the diagnostic parameters for the user.

SUMMARY

In accordance with an aspect of the present disclosure, an ultrasound imaging apparatus includes an image processor configured to generate an ultrasound image based on an ultrasound echo signal; a display; and a main controller configured to detect a liver area and a kidney area in the ultrasound image, extract a border line between the liver area and the kidney area, automatically establish a region of interest of the liver and a region of interest of the kidney based on the border line, obtain a diagnostic parameter for the region of interest of the liver and a diagnostic parameter for the region of interest of the kidney, and control the display to display information about the diagnostic parameter for the region of interest of the liver and the diagnostic parameter for the region of interest of the kidney.

The main controller may establish the region of interest of the liver and the region of interest of the kidney at positions separated by a predetermined distance from the border line.

The main controller may establish the region of interest of the liver and the region of interest of the kidney to be larger than a predetermined reference size.

The main controller may establish the region of interest of the liver and the region of interest of the kidney to have a difference in size less than a predetermined reference value.

The diagnostic parameter may include at least one of a representative gray scale, a distribution of backscattering, and a change in RF signal frequency.

The main controller may calculate representative gray scales of the region of interest of the liver by depth and calculate representative gray scales of the region of interest of the kidney by depth.

The main controller may calculate ratios of the representative gray scales of the region of interest of the liver by depth and the representative gray scales of the region of interest of the kidney by depth.

The main controller may control the display to display the ratios of the representative gray scales by depth on the ultrasound image.

The main controller may control the display to the representative gray scales of the region of interest of the liver by depth and the representative gray scales of the region of interest of the kidney by depth on the ultrasound image.

The main controller may calculate a representative gray scale of the entire region of interest of the liver and calculate a representative gray scale of the entire region of interest of the kidney.

The main controller may perform regression analysis on the representative gray scale of the entire region of interest of the liver and the representative gray scale of the entire region of interest of the kidney.

The main controller may display the representative gray scale of the entire region of interest of the liver and the representative gray scale of the entire region of interest of the kidney along with the results of regression analysis.

The main controller may control the display to display a notification to reacquire the ultrasound image when detection of the liver area or the kidney area has failed.

The ultrasound imaging apparatus may further include an input device configured to receive from a user a selection of an automatic setting mode for automatically establishing the region of interest of the liver and the region of interest of the kidney or a manual setting mode for manually establishing the region of interest of the liver and the region of interest of the kidney.

The main controller may control the display to display windows having the same size and same shape on the ultrasound image when the manual setting mode is selected, and set a position of the window to the region of interest of the liver or the region of interest of the kidney when the position of the window is input from the user.

The main controller may, when the window at the input position contains an area other than the actual liver area or an area other than the actual kidney area, change at least one of position, size, and shape of the window to exclude the area other than the actual liver area or the area other than the actual kidney area.

The main controller may control the display to display at least one of the changed position, size, and shape of the window.

The ultrasound imaging apparatus may further include an input device configured to receive a command from a user to change at least one of position and size of the region of interest of the liver or the region of interest of the kidney.

The main controller may, when a command to change the size of one of the region of interest of the liver and the region of interest of the kidney, change the size of the other one of the region of interest of the liver and the region of interest of the kidney.

In accordance with another aspect of the present disclosure, an ultrasound imaging apparatus includes an image processor configured to generate an ultrasound image based on an ultrasound echo signal; a display; and a main controller configured to detect a first object and a second object in the ultrasound image, extract a border line between the first and second objects, automatically establish a region of interest of the first object and a region of interest of the second object based on the border line, obtain a diagnostic parameter for the region of interest of the first object and a diagnostic parameter for the region of interest of the second object, and control the display to display information about the diagnostic parameter for the region of interest of the first object and the diagnostic parameter for the region of interest of the second object.

In accordance with an aspect of the present disclosure, a control method of an ultrasound imaging apparatus includes obtaining an ultrasound image; detecting a liver area and a kidney area in the ultrasound image; extracting a border line between the liver area and the kidney area; automatically establishing a region of interest of the liver and a region of interest of the kidney based on the border line; obtaining a diagnostic parameter for the region of interest of the liver and a diagnostic parameter for the region of interest of the kidney; and displaying information about the diagnostic parameter for the region of interest of the liver and the diagnostic parameter for the region of interest of the kidney.

The control method may further include receiving from a user a selection of an automatic setting mode for automatically establishing the region of interest of the liver and the region of interest of the kidney or a manual setting mode for manually establishing the region of interest of the liver and the region of interest of the kidney.

The control method may further include displaying windows having the same size and same shape on the ultrasound image when the manual setting mode is selected, and setting a position of the window to the region of interest of the liver or the region of interest of the kidney when the position of the window is input from the user.

The control method may further include, when the window at the input position contains an area other than the actual liver area or an area other than the actual kidney area, changing at least one of position, size, and shape of the window to exclude the area other than the actual liver area or the area other than the actual kidney area.

The control method may further include displaying at least one of the changed position, size, and shape of the window.

The control method may further include receiving a command from a user to change at least one of position and size of the region of interest of the liver or the region of interest of the kidney.

The control method may further include, when a command to change the size of one of the region of interest of the liver and the region of interest of the kidney, changing the size of the other one of the region of interest of the liver and the region of interest of the kidney.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which:

FIG. 18 is a flowchart illustrating a control method of an ultrasound imaging apparatus in an occasion when a first object is a liver and a second object is a kidney, according to an embodiment of the present disclosure.

DETAILED DESCRIPTION OF EXEMPLARY EMBODIMENTS

Figure 1:
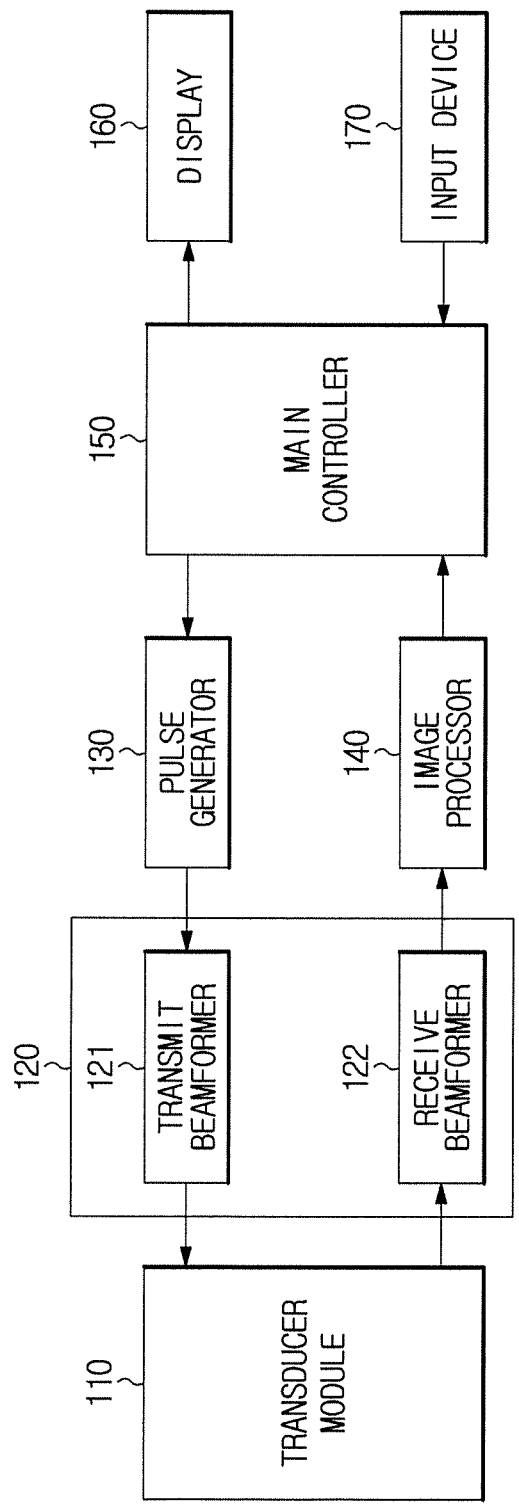
FIG. 1 is a control block diagram of an ultrasound imaging apparatus, according to an embodiment of the present disclosure.

Like numerals refer to like elements throughout the specification. Not all elements of embodiments of the present disclosure will be described, and description of what are commonly known in the art or what overlap each other in the embodiments will be omitted. The terms as used throughout the specification, such as "~ part", "~ module", "~ member", "~ block", etc., may be implemented in software and/or hardware, and a plurality of "~ parts", "~ modules", "~ members", or "~ blocks" may be implemented in a single element, or a single "~ part", "~ module", "~ member", or "~ block" may include a plurality of elements.

It will be further understood that the term "connect" or its derivatives refer both to direct and indirect connection, and the indirect connection includes a connection over a wireless communication network.

The term "include (or including)" or "comprise (or comprising)" is inclusive or open-ended and does not exclude additional, unrecited elements or method steps, unless otherwise mentioned.

Throughout the specification, when a component is mentioned to send or transmit a signal to another component, it does not exclude a possibility of an intermediate component that exists between the two components, through which to send or transmit the signal, unless otherwise mentioned.

It is to be understood that the singular forms "a," "an," and "the" include plural references unless the context clearly dictates otherwise.

Reference numerals used for method steps are just used to identify the respective steps, but not to limit an order of the steps. Thus, unless the context clearly dictates otherwise, the written order may be practiced otherwise.

Embodiments of an ultrasound imaging apparatus and control method thereof will now be described in detail with reference to accompanying drawings.

Figure 2:
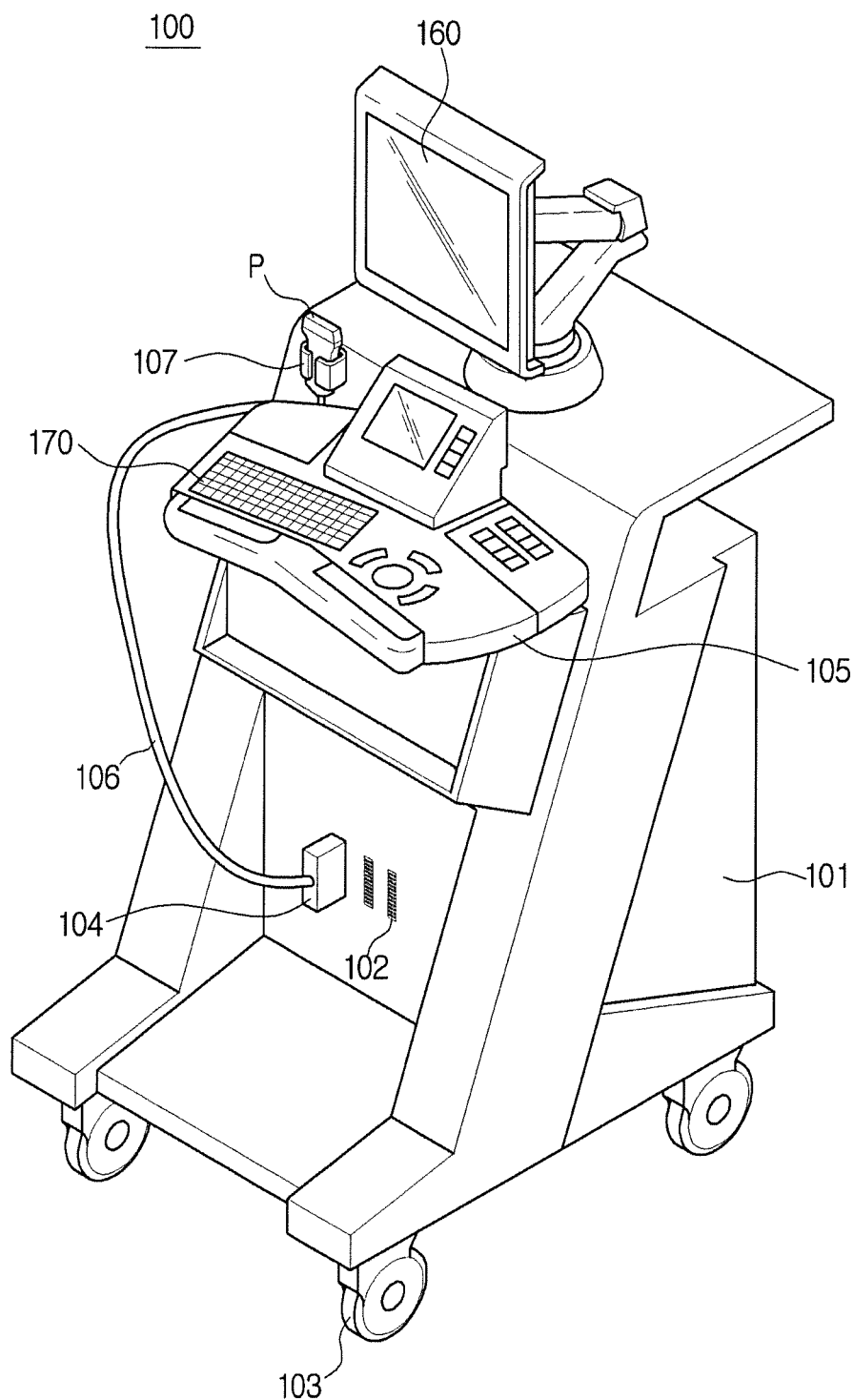
FIG. 2 shows the exterior of an ultrasound imaging apparatus, according to an embodiment of the present disclosure.

FIG. 1 is a control block diagram of an ultrasound imaging apparatus, according to an embodiment of the present disclosure, and FIG. 2 shows the exterior of an ultrasound imaging apparatus, according to an embodiment of the present disclosure.

Referring to both FIGS. 1 and 2, an ultrasound imaging apparatus 100 in accordance with an embodiment includes a transducer module 110 for converting between electrical signals and ultrasound signals, a beamformer 120 for generating transmit beams and receive beams, a pulse controller 130 for generating and sending a control signal for pulse generation to the beamformer 120, an image processor 140 for using an echo signal output from the beamformer 120 to generate an ultrasound image, a main controller 150 for controlling general operation of the ultrasound imaging apparatus 100, a display 160 for displaying the generated ultrasound image and various data required for making a diagnosis, and an input device 170 for receiving inputs from the user.

The transducer module 110 may be provided inside an ultrasonic probe P, which may be connected to a main body 101 of the ultrasound imaging apparatus 100 through a cable 106.

For this, one or more female connectors 102 may be mounted on the lower front of the main body 101. The female connector 102 may be mechanically coupled with a male connector 104 formed at one end of the cable 106.

On the bottom side of the main body 101, there may be multiple casters 103 for mobility of the ultrasound imaging apparatus 100. Using the multiple casters 103, the user may fix or move the ultrasound imaging apparatus 100. Such an ultrasound imaging apparatus 100 may be referred to as a cart-type ultrasonic apparatus.

The main body 101 may have a control panel 105 at the front. The input device 170 may be formed on the control panel 105 to receive an input from the user. The user may input a command to start a diagnosis, select a portion to be diagnosed, select a diagnosis type, select a mode for the ultrasound image, and/or the like, through the input device 170. As an example of the mode for the ultrasound image, there may be Amplitude mode (A mode), Brightness mode (B mode), Color Doppler mode (C mode), Doppler mode (D mode), Elastography mode (E mode), Motion mode (M mode), etc.

The display 160 may be provided on the top of the main body 101. The display 160 may be implemented with at least one of various display panels, such as a Liquid Crystal Display (LCD) panel, Light Emitting Diode (LED) panel, an Organic Light Emitting Diode (OLED) panel, or the like.

Furthermore, the display 160 may be comprised of two or more displays capable of displaying different images at the same time. For example, one of the displays may display a two dimensional (2D) ultrasound image and the other display may display a three dimensional (3D) ultrasound image. In another example, one of the displays may display a B mode image and the other display may display a contrast media image.

There may be one or more probe holders 107 on the outer surface of the main body 101 to hold the ultrasonic probe P. Accordingly, the user may keep the ultrasonic probe P in the probe holder 107 while the ultrasonic probe P is not used.

The beamformer 120 may be provided in the main body 101 or in the probe P. Although the beamformer 120 is shown in the present embodiment as being separated from the probe 100 and provided in the main body 101, embodiments of the ultrasound imaging apparatus 100 are not limited thereto.

The main body 101 may contain the pulse controller 130, the image processor 140, and the main controller 150. The pulse controller 130, the image processor 140, and the main controller 150 may include at least one memory for storing a program for carrying out operations, which will be described later, and at least one processor for executing the program. The pulse controller 130, the image processor 140, and the main controller 150 may use respective memories and processors, or may share some memories and processors.

In the meantime, the exterior of the ultrasound imaging apparatus 100 is not limited to what is shown in FIG. 2. For example, the ultrasound imaging apparatus 100 may be implemented in a portable type. In this case where the ultrasound imaging apparatus 100 is of a portable type, the main body 101 may be shaped like a laptop computer, a portable digital assistant (PDA), a tablet personal computer (PC), etc., and coupled to the ultrasonic probe P to generate ultrasound images.

Figure 3:
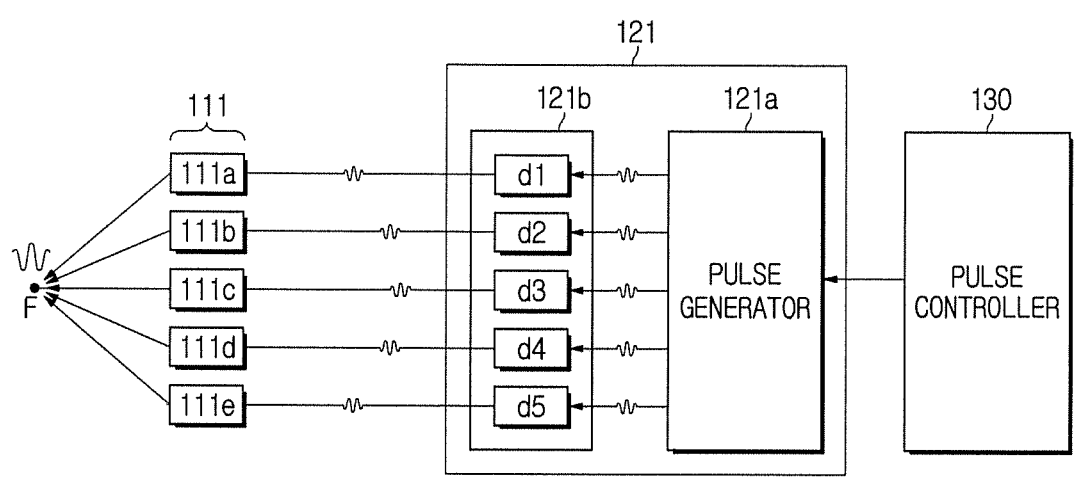
FIG. 3 is a diagram for explaining a procedure of transmitting ultrasound.
Figure 4:
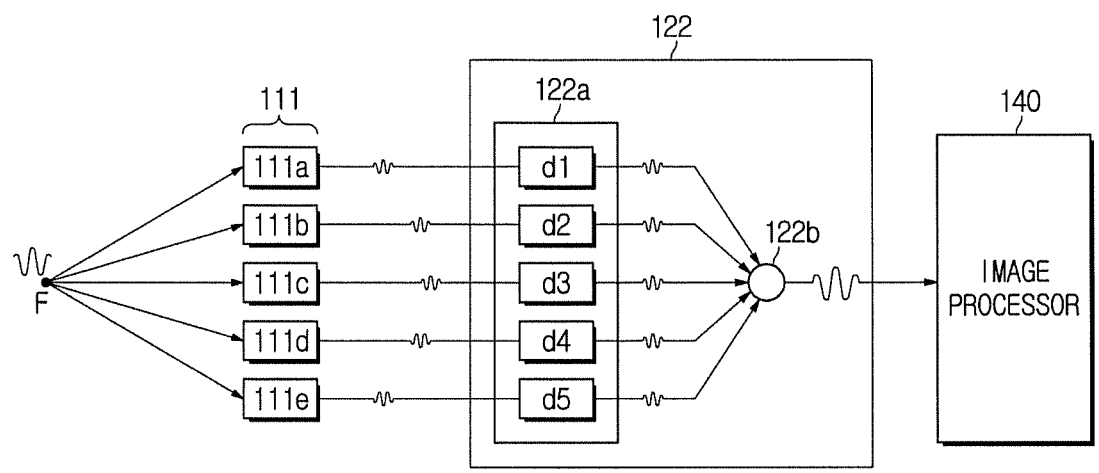
FIG. 4 is a diagram for explaining a procedure of receiving ultrasound.

FIG. 3 is a diagram for explaining a procedure of transmitting ultrasound, and FIG. 4 is a diagram for explaining a procedure of receiving ultrasound.

Referring to FIGS. 3 and 4, the transducer module 110 may include a transducer array 111 having a plurality of transducer elements, and may further include a switch, such as a multiplexer (MUX) for selecting a transducer element to be used in transmitting or receiving an ultrasound signal.

For convenience of explanation, it is assumed in the following embodiment that the transducer array 111 has fiver transducer elements 111$a$, 111$b$, 111$c$, 111$d$, and 111$e$.

The transducer array 111 may convert ultrasound signals to electric signals, and vice versa. For example, the transducer array 111 may be implemented with piezoelectric ultrasonic transducers that use piezoelectric effects. For this, the transducer elements 111$a$ to 111$e$ may include piezoelectric materials or piezoelectric thin films. When an alternate current (AC) current is applied from an internal charger or external power supplier to the piezoelectric material or piezoelectric thin film, the piezoelectric material or piezoelectric thin film vibrates at a certain frequency, which in turn generates a certain frequency of ultrasound depending on the vibration frequency.

On the contrary, when a certain frequency of echo ultrasound reaches the piezoelectric material or piezoelectric thin film, the piezoelectric material or piezoelectric thin film vibrates depending on the frequency of the echo ultrasound and outputs an AC current of a frequency corresponding to the vibration frequency.

It is also possible for the transducer elements 111a to 111e to be implemented with other types of transducers, such as magnetostrictive ultrasonic transducers using magnetostrictive effects of a magnetic substance or capacitive micromachined ultrasonic transducers (cMUTs) that use hundreds or thousands of micromachined thin films to transmit or receive ultrasound.

As shown in FIG. 1, the beamformer 120 may include a transmit beamformer 121 and a receive beamformer 122.

The transmit beamformer 121 performs transmit beamforming. As shown in FIG. 3, distances between a focal point F and the plurality of transducer elements 111a to 111e are different. Accordingly, the transmit beamformer 121 may generate a transmit beam by applying time delays such that ultrasound signals transmitted from the respective transducer elements 111a to 111e reach the focal point F on a transmit scan line at the same time. Since the focused ultrasound signal narrows the ultrasound beam, the resolution in the lateral direction may be enhanced.

The transmit beamformer 121 may include a pulse generator 121a and a first delayer 121b.

The pulse generator 121a generates pulses according to a control signal of the pulse controller 130. For example, the pulses generated by the pulse generator 121a may have a pulse repetition frequency (PRF). The pulses generated by the pulse generator 121a are input to the first delayer 121b.

The first delayer 121b outputs each pulse output from the pulse generator 121a by delaying it by a predefined time. The first delayer 121b may include a plurality of delaying elements d1 to d5 connected to the plurality of transducer elements 111a to 111e, respectively.

The delay time of each delaying element d1 to d5 is determined based on a distance between the corresponding transducer element 111a to 111e and the focal point F. Specifically, each of the second to fourth delaying elements d2 to d4 delays input pulses by a predefined time and outputs the delayed pulses such that ultrasound signals transmitted from the second to fourth transducer elements 111b to 111d reach the focal point F at the same time when the ultrasound signals transmitted from the first and fifth transducer elements 111a and 111e relatively far from the focal point F reach the focal point F.

As described above, the ultrasound transmitted through the transducer array 111 is reflected by an object and entered back into the transducer array 111. Upon receiving the echo ultrasound reflected from the object, each of the transducer elements 111a to 111e outputs an echo signal corresponding to the received echo ultrasound. The echo signal is entered into the receive beamformer 122.

Referring to FIG. 4, the receive beamformer 122 includes a second delayer 122a and a combiner 122b. Although not shown, the receive beamformer 122 may further include a receiver for receiving the echo signal and performing amplification and gain adjustment on the echo signal, or the receive beamformer 122 may further include an analog-to-digital converter (ADC), when implemented digitally, for converting the analog echo signal, which underwent the amplification and gain adjustment, to a digital echo signal.

The second delayer 122a may include a plurality of delaying elements d1 to d5 connected to the plurality of transducer elements 111a to 111e, respectively.

Since the echo ultrasound reaches the transducer elements 111a to 111e at different points of time, the delaying elements d1 to d5 delay the input echo signals to have them focused.

For example, the third delaying element d3, at which the echo signal arrives first, delays the input echo signal until the echo signal is entered into the first and fifth delaying elements d1 and d5.

The combiner 122b combines echo signals output from the respective delaying elements d1 to d5. In this case, the combiner 122b may apply weights to the respective echo signals and combine them.

The image processor 140 generates an ultrasound image based on the echo signal output from the receive beamformer 122. For example, the image processor 140 may generate at least one of A mode image, B mode image, D mode image, E mode image, and M mode image, based on the echo signal. Furthermore, the image processor 140 may generate a 3D ultrasound image based on a plurality of ultrasound images acquired from the echo signals.

The main controller 150 detects first and second objects adjacent to each other in the ultrasound image and extracts a border line between the first and second objects. The main controller 150 may establish regions of interest, i.e., first and second regions of interest of the first and second objects, respectively, based on the extracted border line, and obtain a diagnostic parameter to be used in diagnosing a particular disease of each of the established regions of interest. In this regard, to increase objectivity, reliability, and reproducibility of a diagnosis result by minimizing a deviation of diagnostic parameter between the two regions, caused by other reasons than diseases, the first and second regions of interest may be established to have a size larger than a certain reference and to be the same or similar in size to each other. This will be described in more detail later.

The diagnostic parameters are provided for the user in various forms, which will be described later in detail.

The main controller 150 controls the display 160 to display the ultrasound image generated by the image processor 140 and associated diagnostic parameters.

Figure 5:
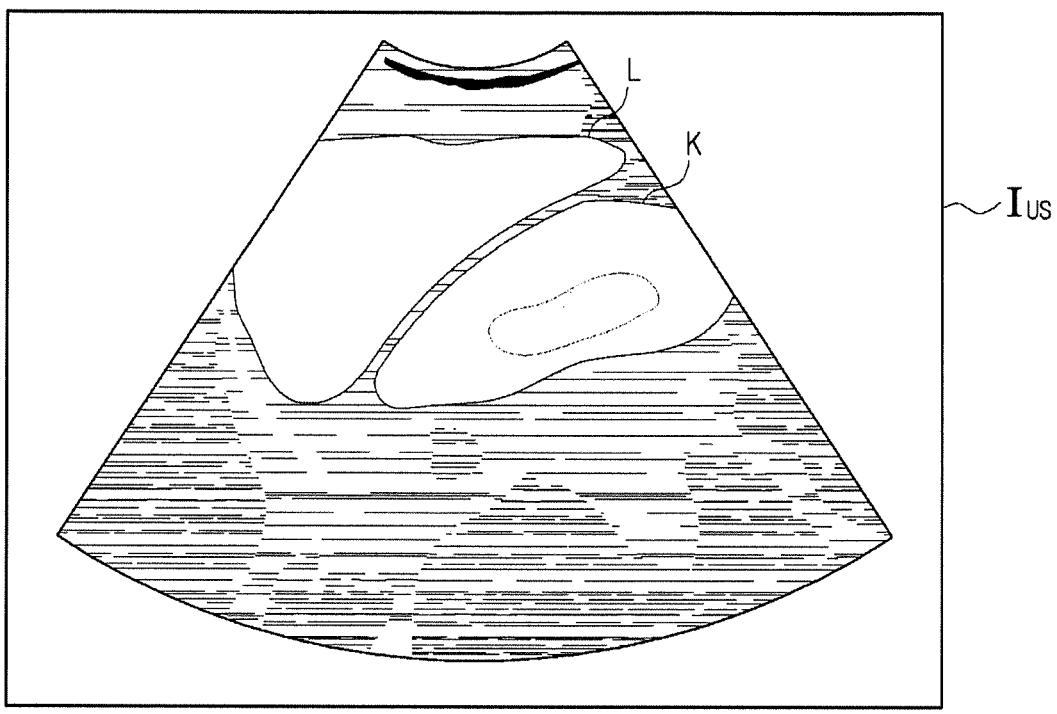
FIG. 5 shows an example of an ultrasound image generated by an ultrasound imaging apparatus, according to an embodiment of the present disclosure.
Figure 6:
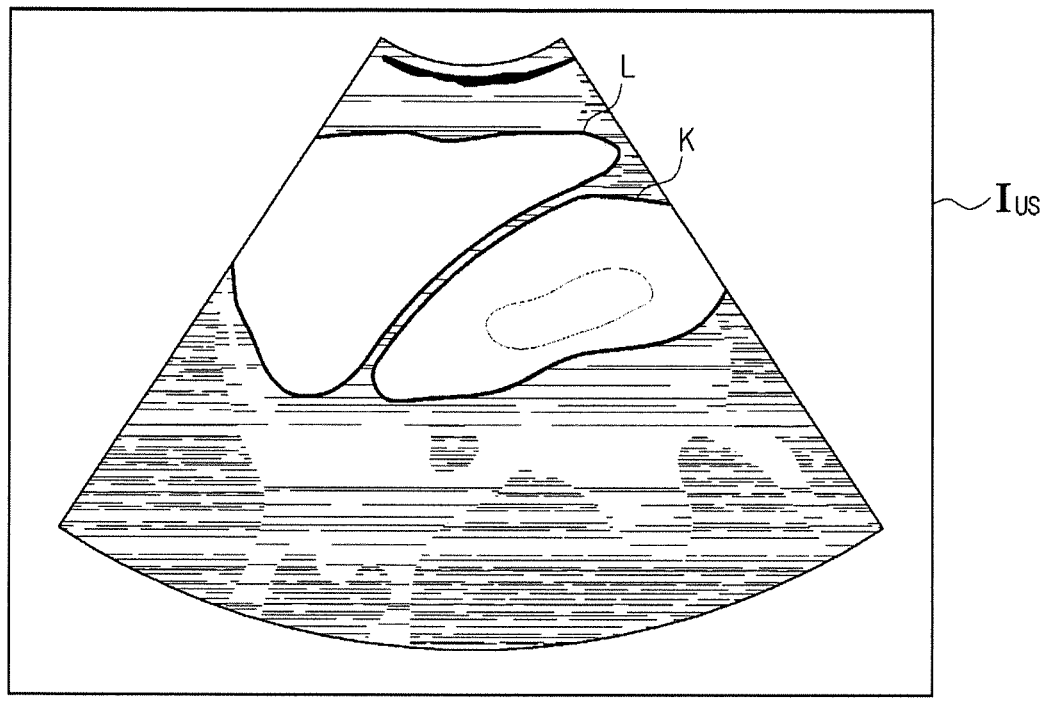
FIG. 6 is a diagram for explaining operation of an ultrasound imaging apparatus detecting particular objects in an ultrasound image, according to an embodiment of the present disclosure.
Figure 7:
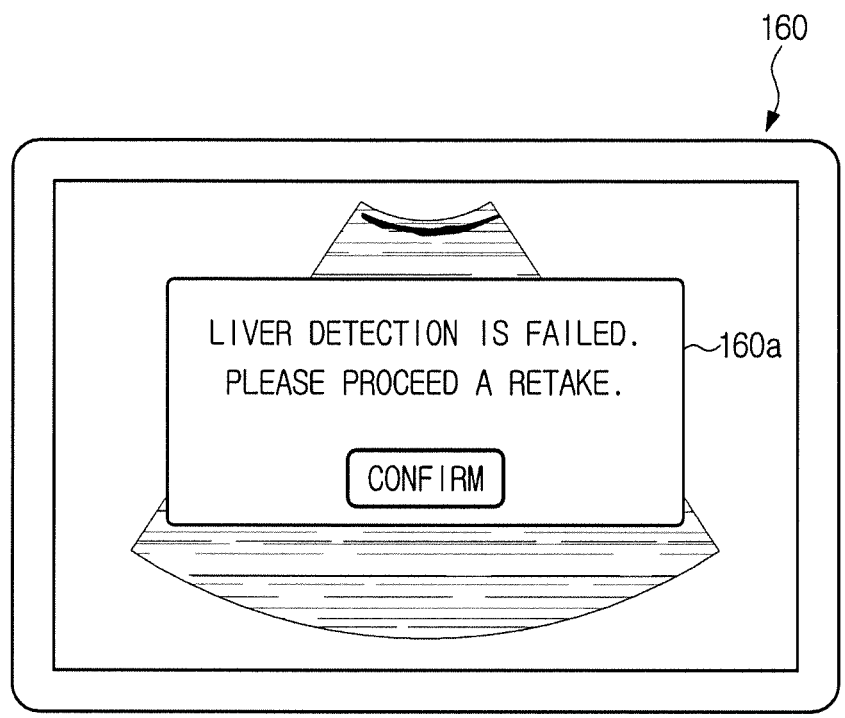
FIG. 7 shows an example of a notification screen displayed in an ultrasound imaging apparatus, according to an embodiment of the present disclosure.

FIG. 5 shows an example of an ultrasound image generated by an ultrasound imaging apparatus, according to an embodiment of the present disclosure, FIG. 6 is a diagram for explaining operation of an ultrasound imaging apparatus detecting particular objects in an ultrasound image, according to an embodiment of the present disclosure, and FIG. 7 shows an example of a notification screen displayed in an ultrasound imaging apparatus, according to an embodiment of the present disclosure.

The user, such as a doctor, may use the ultrasound image displayed on the display 160 to diagnose a particular disease, and a portion from which to obtain an ultrasound image may vary depending on a target disease to be diagnosed. For example, an abdominal ultrasound image may be used in diagnosing a fatty liver.

The fatty liver is a disease caused by fat deposition in the liver, and is known to develop into a steatohepatitis or a hepatic fibrosis, or even into a terminal liver disease such as cirrhosis or hepatocellular carcinoma. Furthermore, since it is reported worldwide that the fatty liver disease is highly prevalent and especially, the disease shows a close link with obesity and metabolic syndrome, detection of a fatty liver is considered very important in ultrasonography.

Referring to FIG. 5, an abdominal ultrasound image $I_{US}$ generated by the ultrasound imaging apparatus 100 may have a liver area L and a neighboring kidney area K. In a case of a normal liver, echo levels in the liver and the kidney cortex are similar, but in a case of a fatty liver, the echo level increases as fats scatter ultrasound beams. Accordingly, comparison of brightness between the liver area L and the kidney area K in the ultrasound image may be used in detecting a fatty liver. For example, if the liver area L is brighter than the kidney area K, the difference in brightness may be diagnosed as the fatty liver.

The user may make a diagnosis with his/her naked eyes by looking at an ultrasound image displayed on the display 160, or may make a diagnosis by designating regions of interest in the ultrasound image through the input device 170 and reviewing a particular diagnostic parameter displayed for the designated regions of interest if the particular diagnostic parameter is displayed.

In the former case, the diagnosis result may depend on the user's proficiency and is hard to be corrected because it is affected by the user's subjective judgment. Even in the latter case where the user designates regions of interest in person, the designated regions of interests may have different sizes and positions without clear references for the size and position of the region of interest, and accordingly, there may be a gray scale deviation.

However, in accordance with an embodiment, the ultrasound imaging apparatus 100 may have increased accuracy and reproducibility of diagnosis by automatically designating regions of interest of the two neighboring objects based on a border line between the two objects and obtaining diagnostic parameters for the respective regions of interest.

In the following description, it will be assumed that the first object is a liver and the second object is a kidney for explaining embodiments in more detail. However, it is only for convenience of explanation, and the embodiment will be equally applied to other various organs.

Referring to FIG. 6, the main controller 150 may detect the liver area L and the kidney area K in the ultrasound image $I_{US}$. For example, the main controller 150 may detect the liver area L and the kidney area K with a feature extraction algorithm or outline extraction algorithm that uses anatomical characteristics of the liver and kidney. It is also possible for the main controller 150 to use machine learning, especially 'deep learning', in detecting the liver area L and kidney area K.

In the meantime, there may be an occasion when the main controller 150 fails to properly detect the liver area or kidney area due to too much noise contained in the ultrasound image or due to an error in the procedure of acquiring the ultrasound image. In this case, the main controller 150 may control the display 160 to display a notification screen 160a notifying a failure of region detection and prompting to reacquire the ultrasound image, as shown in FIG. 7. Accordingly, the possibility of making a wrong diagnosis based on a bad image may be reduced.

Figure 8:
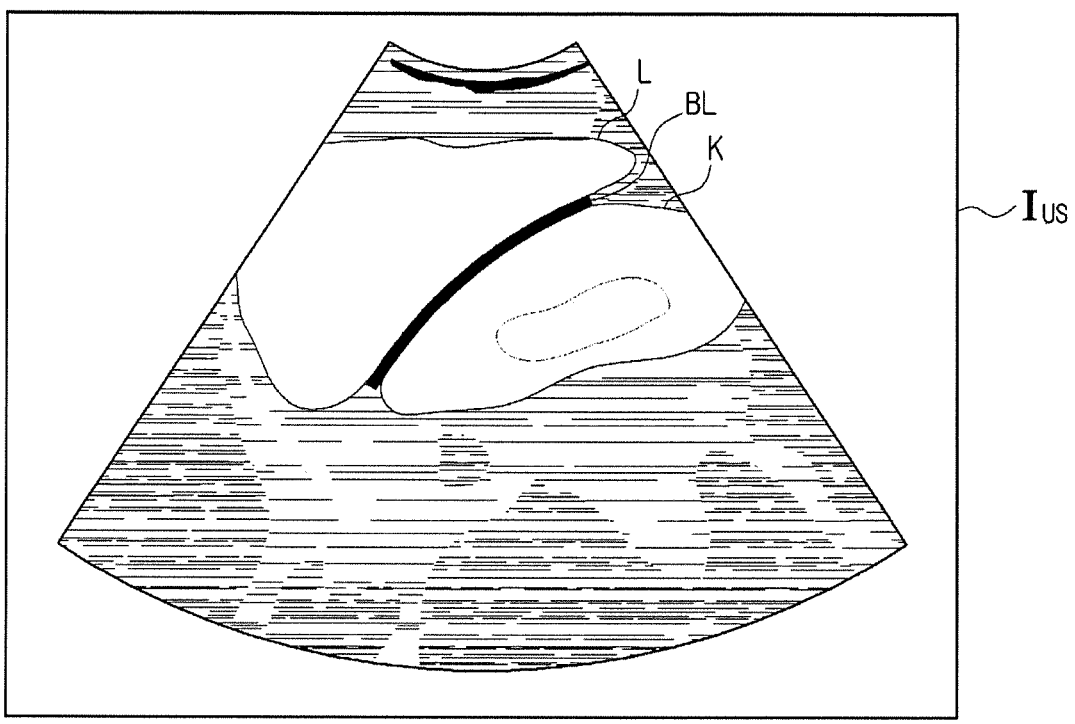
FIG. 8 is a diagram for explaining operation of an ultrasound imaging apparatus extracting a border line between particular objects, according to an embodiment of the present disclosure.
Figure 9:
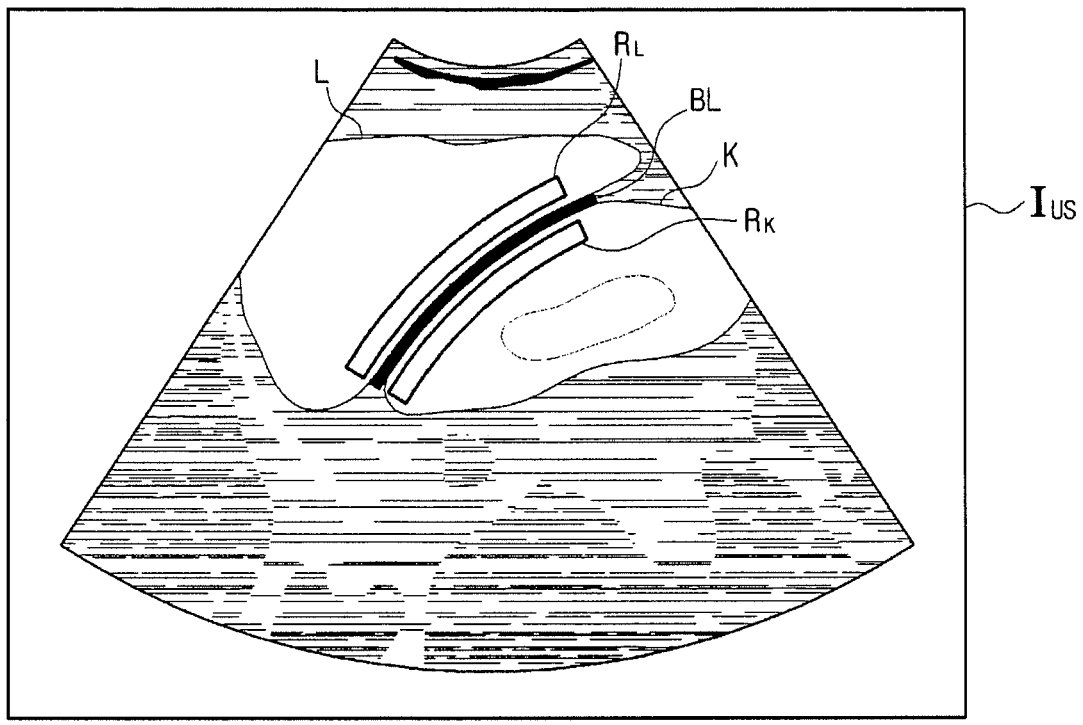
FIG. 9 is a diagram for explaining operation of an ultrasound imaging apparatus establishing regions of interest based on an extracted border line, according to an embodiment of the present disclosure.

FIG. 8 is a diagram for explaining operation of an ultrasound imaging apparatus extracting a border line between particular objects, according to an embodiment of the present disclosure, and FIG. 9 is a diagram for explaining operation of an ultrasound imaging apparatus establishing regions of interest based on an extracted boundary, according to an embodiment of the present disclosure.

The main controller 150 may extract a border line BL between the detected liver area L and kidney area K as shown in FIG. 8, and establish regions of interest RL and RK in the liver area L and kidney area K, respectively, based on the extracted border line BL as shown in FIG. 9. The region of interest of the liver RL and the region of interest of the kidney RK may share the border or may be separated by a certain distance. For example, the regions of interest RL and RK may be separated by a predefined distance from the border liner BL, the predefined distance having a certain range.

Furthermore, the main controller 150 may establish the regions of interest of the liver and kidney RL and RK to have a size larger than a predetermined reference.

In addition, the main controller 150 may establish the regions of interest of the liver and kidney RL and RK to have the same size. Alternatively, the sizes of the two regions of interest may have a difference less than a predetermined reference.

By establishing the two regions of interest to have similar or large sizes, the deviation of diagnostic parameter between the two regions caused by other reasons than diseases may be reduced.

Once the regions of interest of the liver and kidney RL and RK are established, the main controller 150 may obtain diagnostic parameters for the respective regions of interest RL and RK.

Prior to obtaining the diagnostic parameters, the main controller 150 may eliminate other areas than the actual liver and kidney areas from the regions of interest. For example, the main controller 150 may eliminate the non-actual areas included in the region of interest based on features of brightness, morphology, or position of the actual liver and kidney areas. Elimination of the non-actual areas included in the regions of interest, which is performed by the main controller 150, may increase reliability of the diagnostic parameters which will be described later.

Figure 10:
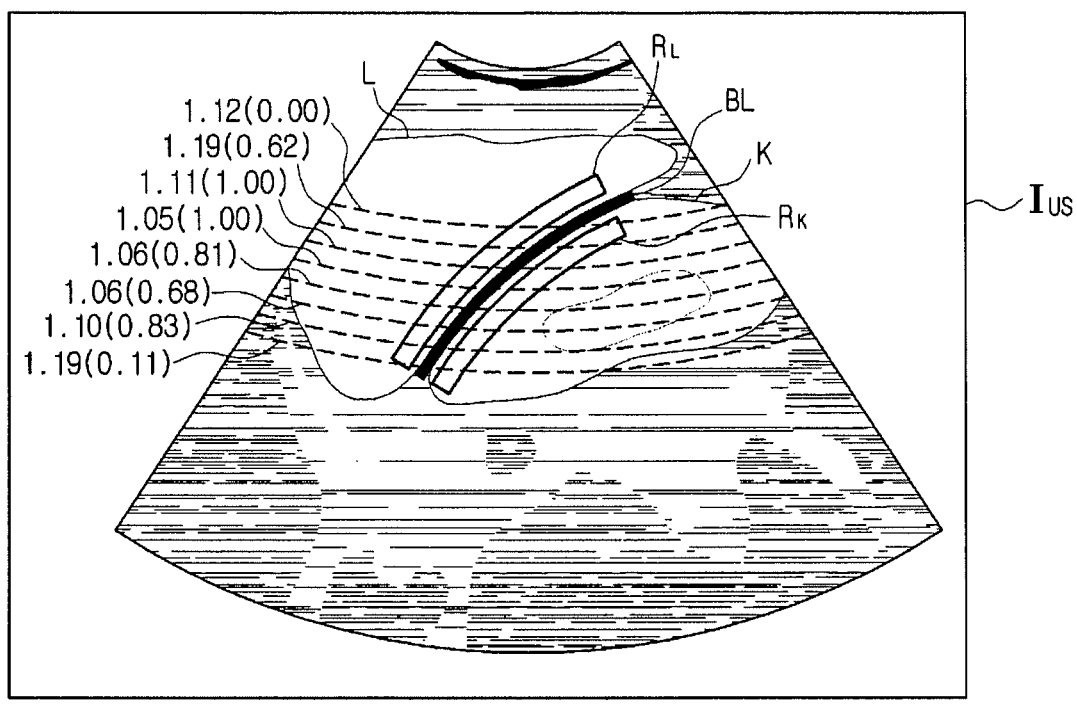
FIGS. 10 and 11 show how an ultrasound imaging apparatus displays diagnostic parameters for regions of interest, according to an embodiment of the present disclosure.
Figure 11:
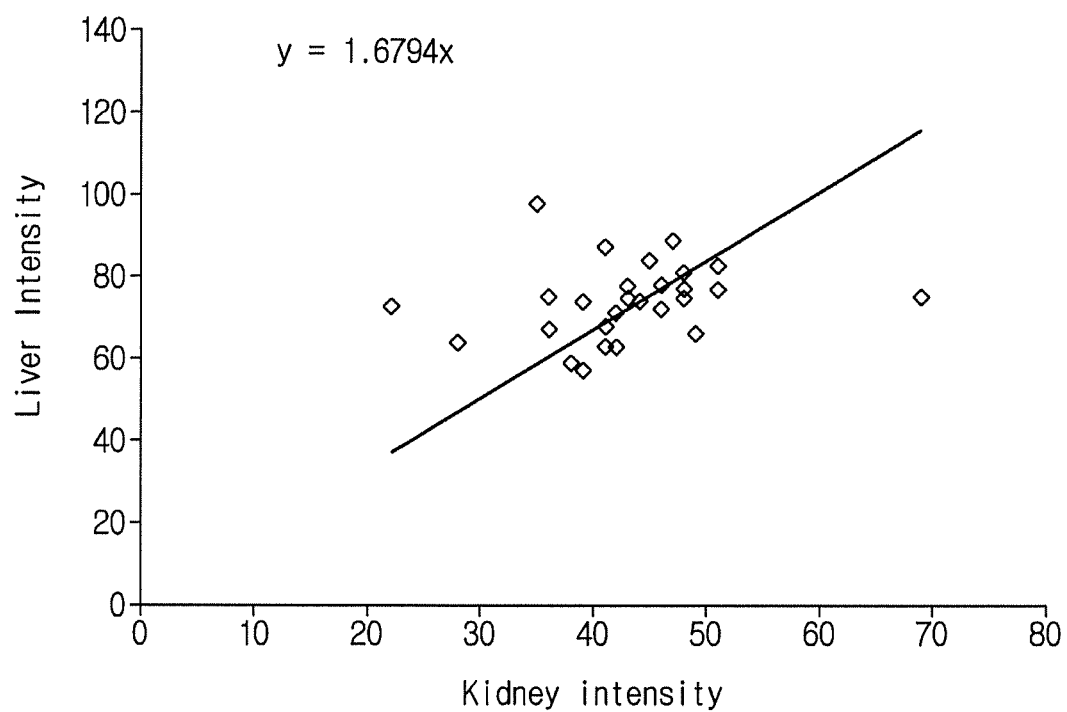

FIGS. 10 and 11 show how an ultrasound imaging apparatus displays diagnostic parameters for regions of interest, according to an embodiment of the present disclosure.

In this embodiment, the diagnostic parameters refer to parameters used in diagnosis for a fatty liver, and may be obtained based on brightness values of the ultrasound image. For example, the main controller 150 may calculate a representative gray scale of the region of interest of the liver and a representative gray scale of the region of interest of kidney, at different depths of the ultrasound image. The representative gray scale may assume an average value or a median value.

Alternatively, the main controller 150 may calculate a distribution of backscattering of the liver and a distribution of backscattering of the kidney at the different depths or calculate ratios of gray scales of the liver and kidney areas at the different depths, and even obtain their reliabilities.

Alternatively, the main controller 150 may calculate a representative gray scale of the entire region of interest of the liver and a representative gray scale of the entire region of interest of the kidney and then a ratio of the representative gray scales of the two regions of interest.

Alternatively, the main controller 150 may calculate distributions of backscattering of the entire region of interest of the liver and the entire region of interest of the kidney, or calculate changes in RF frequency of the entire region of interest of the liver and the entire region of interest of the kidney. The ratio of them may also be calculated.

The main controller 150 may provide the diagnostic parameters for the user in various ways. For example, as shown in FIG. 10, the main controller 150 may control the display 160 to display ratios of representative gray scales of the liver and kidney areas at different depths in the ultrasound image $I_{us}$ and may also display the reliabilities along with the ratios of representative gray scales. The user may check and use the ratios of representative gray scales and reliabilities displayed on the display 160 in diagnosis for fatty liver.

It is also possible to display representative gray scales of the regions of interest of the liver and kidney, respectively, at different depths, or display the distributions of backscattering, or display representative gray scales, distributions of backscattering or changes in RF frequency, and the ratios for the entire regions of interest.

In another example, as shown in FIG. 11, the main controller 150 may control the display 160 to represent the representative gray scales of the regions of interest of the liver and kidney, respectively, at different depths on a graph and also display results of regression analysis on their relations. For example, a straight line, regression formula or slope obtained by the linear regression analysis may also be displayed.

In an embodiment, the ultrasound imaging apparatus 100 may allow the user to select how to establish a region of interest, how to obtain or display a diagnostic parameter, etc. This will be described in detail in connection with FIGS. 12 to 15.

Figure 12:
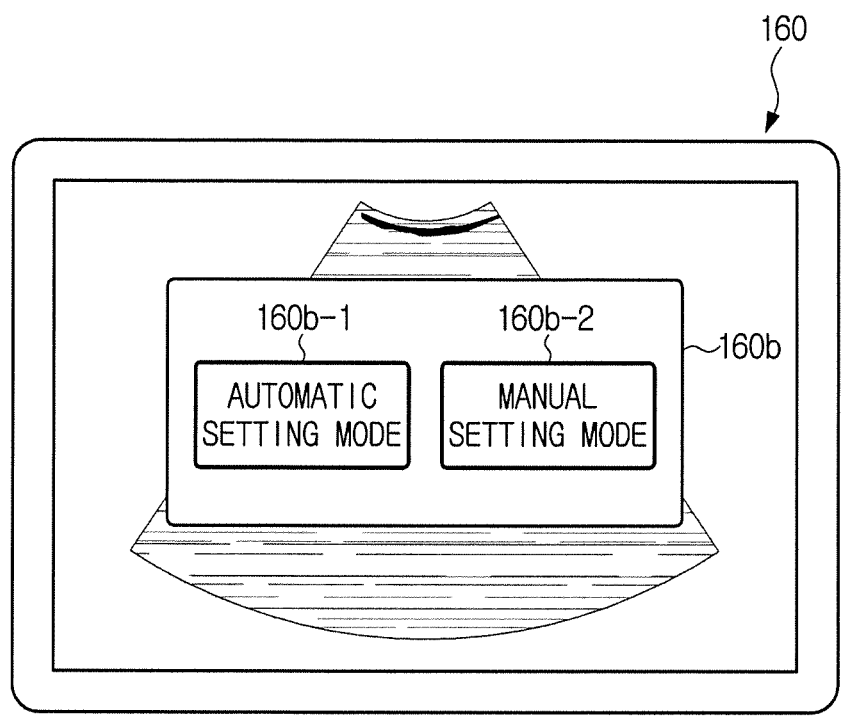
FIG. 12 shows how an ultrasound imaging apparatus receives a selection of a mode for establishing regions of interest, according to an embodiment of the present disclosure.
Figure 13:
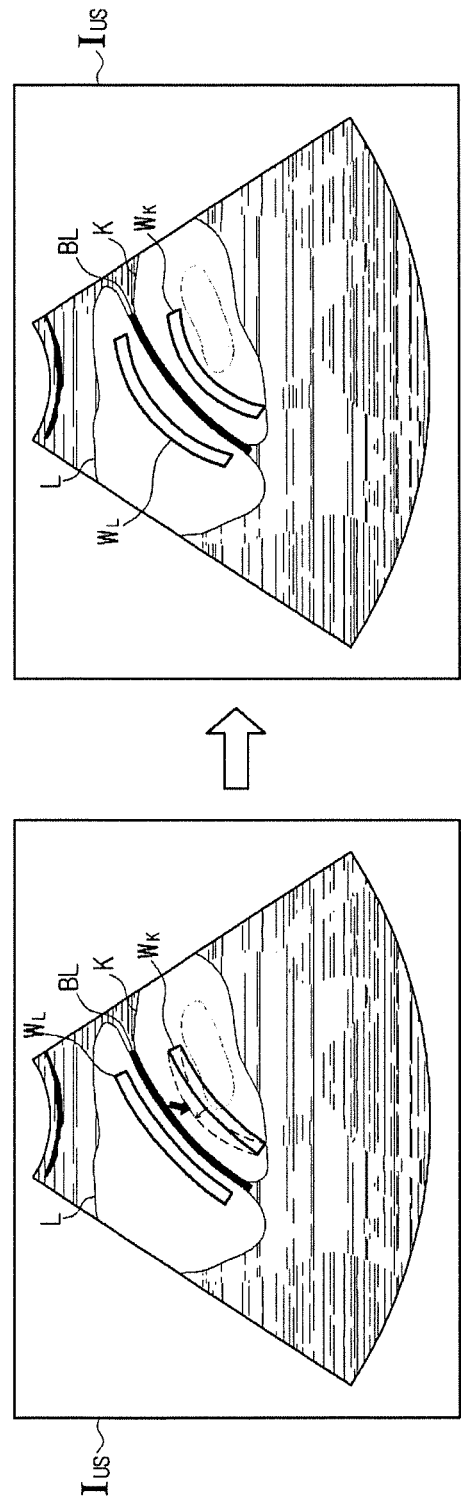
FIG. 13 shows how an ultrasound imaging apparatus receives settings of a region of interest from the user, according to an embodiment of the present disclosure.

FIG. 12 shows how an ultrasound imaging apparatus receives a selection of a mode for establishing regions of interest, according to an embodiment of the present disclosure, and FIG. 13 shows how an ultrasound imaging apparatus receives settings of a region of interest from the user, according to an embodiment of the present disclosure.

Referring to FIG. 12, the main controller 150 may control the display 160 to display a mode selection screen 160b. The mode selection screen 160b may include an automatic setting button 160b-1 to select an automatic setting mode and a manual setting button 160b-2 to select a manual setting mode. When the user inputs a mode selection to the mode selection screen 160b through the input device 170, a region of interest may be established according to the selected mode.

For example, when the user selects the manual setting button 160b-2, the user may establish a region of interest as he/she wants by manipulating the input device 170 in person. For example, when an ultrasound image is displayed on the display 160, a tool for establishing a region of interest may be displayed on the ultrasound image for the user to establish a region of interest.

The tool for establishing a region of interest may provide windows, e.g., $W_L$ and $W_K$, as shown in FIG. 13, having a shape corresponding to a region of interest, in which case the user may input a selection of a region of interest by moving a window displayed on the ultrasound image to an area at which the user intends to establish a region of interest.

In this regard, the main controller 150 may display the windows, e.g., $W_L$ and $W_K$, having the same or similar sizes in the liver and kidney areas, thereby guiding the user to establish a region of interest in an objective and reproducible manner as in an occasion when the main controller 150 automatically establishes regions of interest.

Furthermore, once the user establishes a region of interest, the main controller 150 may determine whether the region of interest contains any non-actual area. When the region of interest established by the user contains the non-actual area, the non-actual area may be excluded from the region of interest by changing the shape, size, or position of the region of interest, as shown in FIG. 13.

In the case of changing the shape or size of the region of interest to exclude the non-actual area from the region of interest, the shape or size of the other region of interest may be correspondingly changed.

Figure 14:
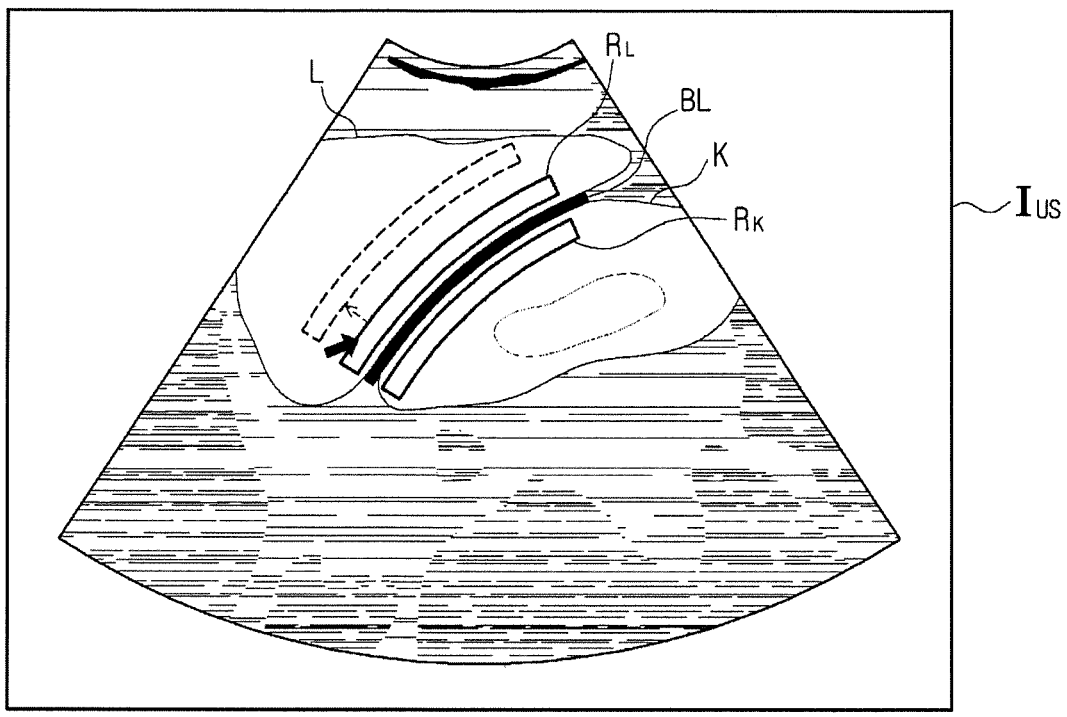
FIGS. 14 and 15 show how an ultrasound imaging apparatus receives a change of a region of interest from the user, according to an embodiment of the present disclosure.
Figure 15:
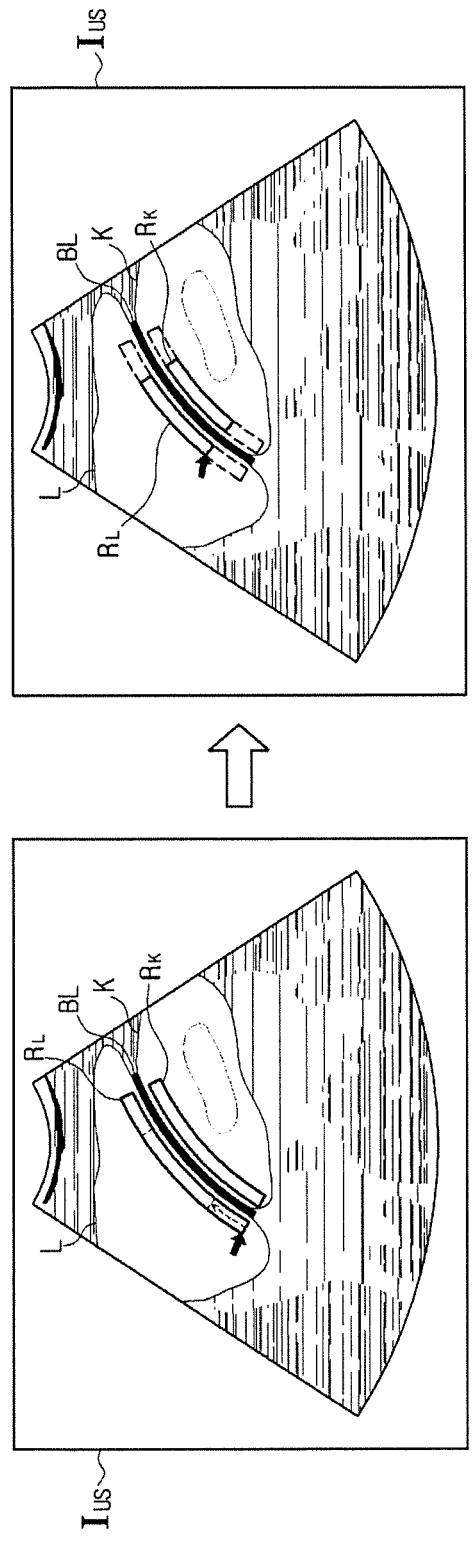

FIGS. 14 and 15 show how an ultrasound imaging apparatus receives a change of a region of interest from the user, according to an embodiment of the present disclosure.

When the user selects the automatic setting button 160b-1 in the embodiment of FIG. 12, the main controller 150 may detect the liver area L and the kidney area K in the ultrasound image, extract a border line between the two areas, and automatically establish regions of interest based on the extracted border line, as described above.

As shown in FIG. 14, when the display 160 displays the regions of interest of the liver RL and kidney RK automatically established by the main controller 150, the user may input a command to change a position of one of the regions of interest through the input device 170.

For example, if the input device 170 includes a mouse, the user may manipulate the mouse to move a cursor displayed on the display 160 onto the region of interest, of which the user intends to change the position, e.g., RL, and click and drag the mouse to a desired position. If the input device 170 includes a touch panel, the user may directly touch the region of interest RL displayed on the display 160 and drag it to a desired position.

Furthermore, as shown in FIG. 15, it is also possible for the user to input a command to change the size of the region of interest RL by manipulating the input device 170. If the user changes the size of one of the two regions of interest RL and RK, the main controller 150 may measure the changed size of the region of interest RL and set the other region of interest RK to have the same or similar size to the changed size of the region of interest RL.

Figure 16:
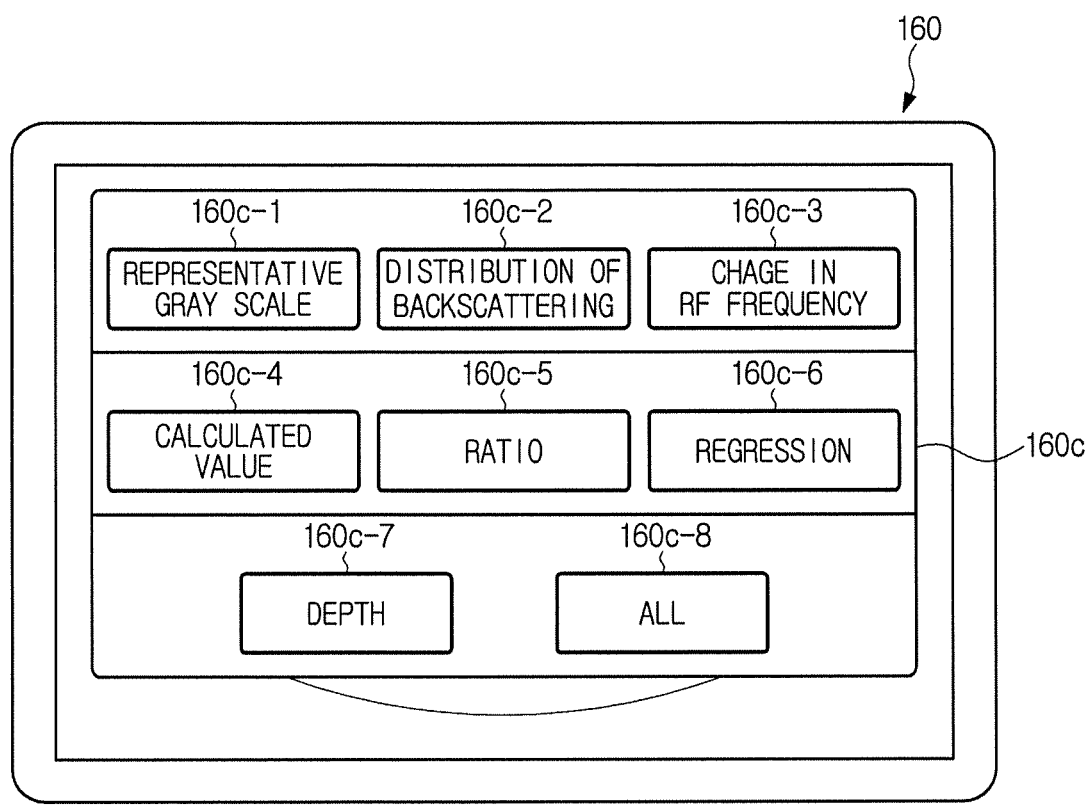
FIG. 16 shows an example of a selection of diagnostic parameters received by an ultrasound imaging apparatus, according to an embodiment of the present disclosure.

FIG. 16 shows an example of a selection of diagnostic parameters received by an ultrasound imaging apparatus, according to an embodiment of the present disclosure.

As described above, once the regions of interest are established, the main controller 150 obtains diagnostic parameters for the established regions of interest. The diagnostic parameters may be set and obtained by default. Alternatively, as shown in FIG. 16, the display 160 may display a diagnostic parameter selection screen 160c from which to select diagnostic parameters and allow the user to input a selection of diagnostic parameters to be obtained by the main controller 150 or displayed by the display 160.

For example, the diagnostic parameter selection screen 160c may include a plurality of buttons to select types of the diagnostic parameters, a plurality of buttons to select methods for providing the diagnostic parameters, and a plurality of buttons to select regions for obtaining the diagnostic parameters.

The plurality of buttons to select types of the diagnostic parameters may include buttons 160c-1, 160c-2, and 160c-3 corresponding to representative gray scale, distribution of backscattering, change in RF frequency, respectively, and the plurality of buttons to select methods for providing the diagnostic parameters may include buttons 160c-4, 160c-5, and 160c-6 corresponding to calculated value, ratio, and regression. Furthermore, the plurality of buttons to select regions for obtaining the diagnostic parameters may include buttons 160c-7 and 160c-8 corresponding to obtaining the diagnostic parameters by depth and for the whole region, respectively.

If the user selects the representative gray scale button 160c-1, ratio button 160c-5, and depth button 160c-7, the main controller 150 may calculate representative gray scales of the regions of interest of the liver and kidney RL and RK by depth and calculate the ratio of the representative gray scales of the regions of interest between the liver and the kidney. The main controller 150 may control the display 160 to display the calculated ratio of the representative gray scales and also display the reliability of the calculated ratio if the reliability is calculated.

If the user selects the representative gray scale button 160c-1, calculated value button 160c-4, and depth button 160c-7, the main controller 150 may calculate representative gray scales of the regions of interest of the liver and kidney RL and RK by depth and control the display 160 to display the calculated representative gray scales by depth.

A control method of an ultrasound imaging apparatus in accordance with an embodiment will now be described in detail. The control method of an ultrasound imaging apparatus may be performed by the ultrasound imaging apparatus 100 according to the previous embodiments. Accordingly, what are described above with reference to FIGS. 1 to 16 may also be applied in the control method of the ultrasound imaging apparatus without being specifically mentioned.

Figure 17:
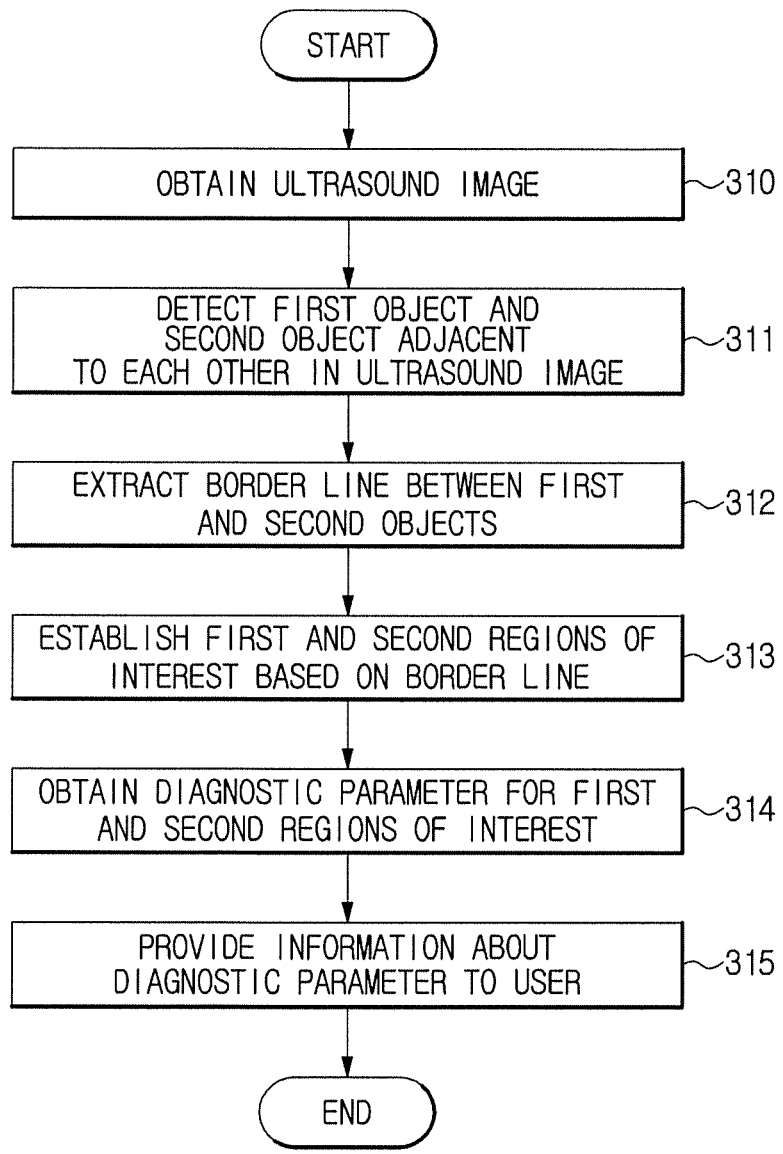
FIG. 17 is a flowchart illustrating a control method of an ultrasound imaging apparatus, according to an embodiment of the present disclosure.

FIG. 17 is a flowchart illustrating a control method of an ultrasound imaging apparatus, according to an embodiment of the present disclosure.

The control method of the ultrasound imaging apparatus starts with obtaining an ultrasound image, in 310. The portion from which to obtain the ultrasound image may be changed depending on the target to be diagnosed. The ultrasound image may be generated in any of A mode, B mode, D mode, E mode, and M mode having different characteristics, but in the following description, it is assumed that the ultrasound image is generated as a B mode image.

First and second objects adjacent to each other in the ultrasound image are detected in 311, and a border line between the first and second objects is extracted in 312. The first and second objects are substances included inside the target for examination. For example, if the target for examination is a human body, the first and second objects may be some organs in the human body. For example, the main controller 150 may detect the first and second objects with a feature extraction algorithm or outline extraction algorithm that uses anatomical characteristics of the first and second objects.

First and second regions of interest are established based on the border line, in 313. In this regard, to increase objectivity, reliability, and reproducibility of a diagnosis result by minimizing a deviation of diagnostic parameters between the two regions caused by other reasons than diseases, the first and second regions of interest may be established to have a size larger than a certain reference and to be the same or similar in size to each other.

Diagnostic parameters of the first and second regions of interest are calculated in 314, and information about the calculated diagnostic parameters are provided to the user in 315. The diagnostic parameters may include representative gray scales, distributions of backscattering, changes in RF frequency, etc., and the main controller 150 may calculate at least one of the various diagnostic parameters. The calculated diagnostic parameters may be provided for the user by being displayed on the display 160, in which case, the calculated values, the ratio of them, or the result of regression analysis may be displayed on the ultrasound image.

FIG. 18 is a flowchart illustrating a control method of an ultrasound imaging apparatus in an occasion when a first object is a liver and a second object is a kidney, according to an embodiment of the present disclosure.

The control method of the ultrasound imaging apparatus starts with obtaining an ultrasound image, in 320. As described above, a fatty liver may be diagnosed using an abdominal ultrasound image including a liver and a kidney. In other words, to diagnose a fatty liver, an abdominal ultrasound image may be acquired to include a liver and a kidney.

A liver area and a kidney area, which are adjacent to each other, are detected from the ultrasound image in 321, and a border line between the liver area and the kidney area is extracted in 322. In a case of a normal liver, echo levels in the liver and the kidney cortex are similar, but in a case of a fatty liver, the echo level increases as fats scatter ultrasound beams. Accordingly, comparison of brightness between the liver area L and the kidney area K in the ultrasound image may be used in detecting a fatty liver.

The main controller 150 may detect the liver area and the kidney area by using anatomical characteristics of the liver and kidney. However, there may be an occasion when the main controller 150 fails to properly detect the liver area or kidney area due to too much noise contained in the ultrasound image or due to an error in the procedure of acquiring the image. In this case, the main controller 150 may guide a retake by controlling the display 160 to display a notification screen that notifies a failure of region detection and prompts to reacquire an ultrasound image.

A region of interest of each of the liver and kidney is established based on the border line, in 323. The region of interest of the liver RL and the region of interest of the kidney RK may share the border or may be separated by a certain distance.

Furthermore, the main controller 150 may establish the regions of interest of the liver and kidney RL and RK to be larger than a predetermined reference size. In addition, the main controller 150 may establish the regions of interest of the liver and kidney RL and RK to have the same size. Alternatively, the sizes of the two regions of interest may have a difference less than a predetermined reference. By establishing the two regions of interest to have similar or large sizes, the deviation of diagnostic parameter between the two regions caused by other reasons than diseases may be reduced.

The display 160 may display the regions of interest of the liver and kidney RL and RK, which are automatically established by the main controller 150, allowing the user to input a change of the position or size of the regions of interest. Furthermore, if the user changes the size of one, e.g., RL, of the two regions of interest RL and RK, the main controller 150 may measure the changed size of the region of interest RL and set the other region of interest RK to have the same or similar size to the changed size of the region of interest RL.

Diagnostic parameters of the regions of interest of the liver and kidney are calculated, in 324. In this embodiment, the diagnostic parameters refer to parameters used in diagnosis for a fatty liver, and may be obtained based on brightness values of the ultrasound image. For example, the main controller 150 may calculate a representative gray scale of the region of interest of the liver and a representative gray scale of the region of interest of kidney, at different depths of the ultrasound image. The representative gray scale may assume an average value or a median value.

Alternatively, the main controller 150 may calculate a distribution of backscattering of the liver and a distribution of backscattering of the kidney at the different depths or calculate ratios of gray scales of the liver and kidney areas at the different depths, and even obtain their reliabilities.

Alternatively, the main controller 150 may calculate a representative gray scale of the entire region of interest of the liver and a representative gray scale of the entire region of interest of the kidney and then a ratio of the representative gray scales of the two regions of interest.

Alternatively, the main controller 150 may calculate distributions of backscattering of the entire region of interest of the liver and the entire region of interest of the kidney, or calculate changes in RF frequency of the entire region of interest of the liver and the entire region of interest of the kidney. The ratio of them may also be calculated.

The diagnostic parameters may be set and obtained by default. Alternatively, as shown in FIG. 16, the display 160 may display a diagnostic parameter selection screen 160c from which to select diagnostic parameters and allow the user to input a selection of diagnostic parameters to be obtained by the main controller 150 or displayed by the display 160.

Information about the obtained diagnostic parameters are provided to the user, in 325. The main controller 150 may provide the diagnostic parameters obtained by the main controller 150 for the user in various ways. For example, as described above in connection with FIG. 10, the main controller 150 may control the display 160 to display ratios of representative gray scales of the liver and kidney areas at different depths in the ultrasound image $I_{us}$ and may also display the reliabilities along with the ratios of representative gray scales. The user may check and use the ratios of representative gray scales and reliabilities displayed on the display 160 in diagnosis for fatty liver.

It is also possible to display representative gray scales of the regions of interest of the liver and kidney, respectively, at different depths, or display the distributions of backscattering, or display representative gray scales, distributions of backscattering or changes in RF frequency, and the ratios for the entire regions of interest.

In another example, as shown in FIG. 11, the main controller 150 may control the display 160 to represent the representative gray scales of the regions of interest of the liver and kidney, respectively, at different depths on a graph and also display results of regression analysis on their relations.

As described above, it is also possible for the user to select a method for providing the diagnostic parameter.

In an embodiment of the control method of an ultrasound imaging apparatus, the user may input a selection of the automatic setting mode or the manual setting mode.

When the automatic setting mode is selected, the regions of interest are automatically established and the diagnostic parameters are automatically obtained as described above, and when the manual setting mode is selected, the user may input a selection of the region of interest by moving a window displayed on the ultrasound image to an area at which the user intends to establish the region of interest.

In this regard, with the windows, e.g., $W_L$ and $W_K$, having the same or similar sizes displayed in the liver and kidney areas, the user may be guided to establish regions of interest in an objective and reproducible manner as in an occasion when the main controller 150 automatically establishes regions of interest.

Furthermore, once the user establishes a region of interest, the main controller 150 may determine whether the region of interest contains any non-actual area. When the region of interest established by the user contains the non-actual area, the non-actual area may be excluded from the region of interest by changing the shape, size, or position of the region of interest.

In the case of changing the shape or size of the region of interest to exclude the non-actual area from the region of interest, the shape or size of the other region of interest may be correspondingly changed.

According to the embodiments of the present disclosure, an ultrasound imaging apparatus and control method thereof may improve diagnostic reproducibility and accuracy in diagnosing a fatty liver based on an ultrasound image by automatically establishing a region of interest of a liver appearing in the ultrasound image and a region of interest of another internal organ to be compared with the liver, automatically calculating diagnostic parameters for the respective regions of interest, and providing the diagnostic parameters for the user.

Furthermore, in establishing the regions of interest, the sizes of the two regions may be set to be the same or similar or to be larger than a certain reference size so that the deviation of diagnostic parameter between the two regions caused by other reasons than diseases may be minimized to increase objectivity, reliability, and reproducibility.

In addition, various user interfaces (UIs) are provided for the user to select an automatic setting mode or a manual setting mode. When the automatic setting mode is selected, the UI may allow the user to change the automatically established region of interest, thereby reflecting the user's request, and when the manual setting mode is selected, an error of the manually established region may be automatically corrected, thereby increasing objectivity and accuracy in diagnosis.

Several embodiments have been described above, but a person of ordinary skill in the art will understand and appreciate that various modifications can be made without departing the scope of the present disclosure. Thus, it will be apparent to those ordinary skilled in the art that the true scope of technical protection is only defined by the following claims.

What is claimed is:

1. An ultrasound imaging apparatus comprising:
an image processor configured to generate an ultrasound image based on an ultrasound echo signal;
a display;
a main controller configured to:
   detect a liver area and a kidney area in the ultrasound image;
   extract a border line between the liver area and the kidney area;
   automatically establish a region of interest of the liver and a region of interest of the kidney based on the border line;
   obtain a diagnostic parameter for the region of interest of the liver and a diagnostic parameter for the region of interest of the kidney; and
   control the display to display information about the diagnostic parameter for the region of interest of the liver and the diagnostic parameter for the region of interest of the kidney; and
an input device configured to receive a first command for obtaining the diagnostic parameters for the region of interest of the liver and for the region of interest of the kidney by depth;
wherein the diagnostic parameters comprise at least one of a representative gray scale, a distribution of backscattering, or a change in Radio Frequency (RF) signal frequency;
wherein, in response to receiving the first command for obtaining the diagnostic parameters by depth, the main controller is further configured to:

calculate a representative gray scale of the region of interest of the liver by depth and a representative gray scale of the region of interest of the kidney by depth, calculate ratios of the representative gray scale of the region of interest of the liver by depth to the representative gray scale of the region of interest of the kidney by depth, and control the display to display the calculated ratios on the ultrasound image;

wherein the region of interest of the liver has different representative gray scale values by depth and the region of interest of the kidney has different representative gray scale values by depth; and wherein the display is further configured to display the calculated ratios of the representative gray scale values of the region of interest of the liver to the respective representative gray scale values of the region of interest of the kidney and reliabilities of the calculated ratios as the diagnostic parameters.

2. The ultrasound imaging apparatus of claim 1, wherein the main controller is configured to establish the region of interest of the liver and the region of interest of the kidney at positions separated by a predetermined distance from the border line.

3. The ultrasound imaging apparatus of claim 1, wherein the main controller is configured to establish the region of interest of the liver and the region of interest of the kidney to be larger than a predetermined reference size.

4. The ultrasound imaging apparatus of claim 1, wherein the main controller is configured to establish the region of interest of the liver and the region of interest of the kidney to have a difference in size less than a predetermined reference value.

5. The ultrasound imaging apparatus of claim 1, wherein the main controller is configured to control the display to display the representative gray scale of the region of interest of the liver by depth and the representative gray scale of the region of interest of the kidney by depth on the ultrasound image.

6. The ultrasound imaging apparatus of claim 1, wherein the main controller is configured to calculate a representative gray scale of the entire region of interest of the liver and calculate a representative gray scale of the entire region of interest of the kidney.

7. The ultrasound imaging apparatus of claim 1, wherein the main controller is configured to control the display to display a notification to reacquire the ultrasound image when detection of the liver area or the kidney area is failed.

8. The ultrasound imaging apparatus of claim 1, wherein the input device is further configured to receive from a user a selection of an automatic setting mode for automatically establishing the region of interest of the liver and the region of interest of the kidney or a manual setting mode for manually establishing the region of interest of the liver and the region of interest of the kidney.

9. The ultrasound imaging apparatus of claim 8, wherein the main controller is configured to control the display to display windows having the same size and same shape on the ultrasound image when the manual setting mode is selected, and set a position of the windows to the region of interest of the liver or the region of interest of the kidney when the position of the windows is input from the user.

10. The ultrasound imaging apparatus of claim 9, wherein the main controller is configured to, when the windows at the input position contain areas other than the actual liver area or an area other than the actual kidney area, change at least one of position, size, and shape of the windows to exclude the areas other than the actual liver area or the area other than the actual kidney area.

11. The ultrasound imaging apparatus of claim 1, wherein the input device is configured to receive a second command from a user to change at least one of position and size of the region of interest of the liver or the region of interest of the kidney.

12. The ultrasound imaging apparatus of claim 11, wherein the main controller is configured to, when a command to change the size of one of the region of interest of the liver or the region of interest of the kidney, change the size of the other one of the region of interest of the liver or the region of interest of the kidney.

13. A control method of an ultrasound imaging apparatus, the control method comprising:

obtaining an ultrasound image;

detecting a liver area and a kidney area in the ultrasound image;

extracting a border line between the liver area and the kidney area;

automatically establishing a region of interest of the liver and a region of interest of the kidney based on the border line;

obtaining a diagnostic parameter for the region of interest of the liver and a diagnostic parameter for the region of interest of the kidney; and displaying information about the diagnostic parameter for the region of interest of the liver and the diagnostic parameter for the region of interest of the kidney;

wherein the diagnostic parameter comprises at least one of a representative gray scale, a distribution of backscattering, or a change in Radio Frequency (RF) signal frequency;

wherein the obtaining of the diagnostic parameter for the region of interest of the liver and a diagnostic parameter for the region of interest of the kidney comprises, in response to receiving the command for obtaining the diagnostic parameter by depth:

calculating a representative gray scale of the region of interest of the liver by depth; and calculate a representative gray scale of the region of interest of the kidney by depth; and calculating ratios of the representative gray scale of the region of interest of the liver by depth to the representative gray scale of the region of interest of the kidney by depth; and displaying of information about the diagnostic parameter for the region of interest of the liver and the diagnostic parameter for the region of interest of the kidney comprises displaying the calculated ratios the ultrasound image;

wherein the region of interest of the liver has different representative gray scale values by depth and the region of interest of the kidney has different representative gray scale values by depth; and wherein the display displays as the information about the diagnostic parameters the calculated ratios of the representative gray scale values of the region of interest of the liver to the respective representative gray scale values of the region of interest of the kidney along with reliabilities of the calculated ratios.

14. The control method of claim 13, further comprising receiving from a user a selection of an automatic setting mode for automatically establishing the region of interest of the liver and the region of interest of the kidney or a manual setting mode for manually establishing the region of interest of the liver and the region of interest of the kidney.

15. The control method of claim 14, further comprising: displaying windows having the same size and same shape when the manual setting mode is selected; and setting a position of the window to the region of interest of the liver or the region of interest of the kidney when the position of the windows is input from the user.

* * * * *